United States Patent [19]

Amor et al.

[11] Patent Number: 4,723,259
[45] Date of Patent: Feb. 2, 1988

[54] COMPUTED TOMOGRAPHY MOTOR

[75] Inventors: William H. Amor, Chagrin Falls; John Dobbs, Broadview Heights; Anton Z. Zupancic, Kirtland; Robert E. Levar, Willoughby, all of Ohio

[73] Assignee: Picker International Inc., Highland Heights, Ohio

[21] Appl. No.: 668,426

[22] Filed: Nov. 5, 1984

[51] Int. Cl.$^4$ .................. A61B 6/00; H05G 1/60; G01T 1/00
[52] U.S. Cl. ........................... 378/10; 378/4; 378/15
[58] Field of Search .............. 378/4, 10, 15, 197, 378/198

[56] References Cited

U.S. PATENT DOCUMENTS

| | | |
|---|---|---|
| 4,093,862 | 6/1978 | Brandt et al. |
| 4,139,775 | 2/1979 | Williams |
| 4,200,797 | 4/1980 | Bax |
| 4,227,088 | 10/1980 | Maydan et al. |
| 4,365,339 | 12/1982 | Pavkovich et al. |
| 4,402,085 | 8/1983 | Distler et al. |

FOREIGN PATENT DOCUMENTS 2744125 5/1979 Fed. Rep. of Germany .
57-189558 2/1983 Japan .
965423A 6/1978 U.S.S.R. .

OTHER PUBLICATIONS

Engineering drawing of a prior art Induction Motor design used in Picker International's Synerview 1200 computed tomography scanner.

Primary Examiner—Carolyn E. Fields
Assistant Examiner—Joseph A. Hynds
Attorney, Agent, or Firm—Watts, Hoffmann, Fisher & Heinke Co.

[57] ABSTRACT

A computed tomography motor forming an integral part of the scanning apparatus. Motor laminations are mounted to a stationary computed tomography gantry while motor magnets are mounted directly and onto the cylindrical surface of a rotating race member opposite the field the field generating means to rotate with a rotatable computed tomography frame. Energization of the motor laminations cause relative movement between frame and gantry thereby causing an X-ray tube supported by the frame to rotate with the respect to a subject of interest.

6 Claims, 6 Drawing Figures

COMPUTED TOMOGRAPHY MOTOR

Technical Field

The present invention relates to computed tomography (CT) and more particularly to a motor for imparting scanning motion to a computed tomography scanner.

BACKGROUND ART

In computed tomography, a patient's or subject's cross-section of interest is successively scanned from a number of directions by an x-radiation source to direct X-rays through the cross-section of interest. One or more detectors positioned on an opposite side of the patient obtain intensity readings of the x-radiation after it has passed through the patient. If enough intensity measurements from different directions are obtained, these intensity readings can be utilized to reconstruct a density mapping of the patient's cross-section.

Computed tomography reconstruction techniques are derived from mathematical reconstruction algorithms utilizing the fact that each radiation intensity reading corresponds to a line integral of an attenuation function taken through the patient from the source to the position the intensity is sensed. These reconstruction algorithms allocate this attenuation along the path the radiation takes in traversing the patient in a process known as back projection.

Fourth generation computed tomography designs include a circular array of stationary detectors and a moving x-radiation source. The fourth generation array of detectors typically surrounds a patient aperture which defines a patient scanning plane. An X-ray source then radiates the plane from a number of spaced locations. This scanning is typically achieved by orbiting an X-ray tube about the patient and detecting X-ray intensities of radiation passing through the patient.

In early and current third generation computed tomography scanner designs the detectors also move as the patient is scanned. In orbital CT designs, for example, the X-ray source and an arc of detectors orbit in unison about the patient.

A common need in all commercial computed tomography scanners known to applicants is a motive force for moving at least the X-ray source and in some designs both the source and detectors. Heretofore, this motive force was often provided by a motor coupled to a support for the X-ray tube via either a belt or gear linkage.

Such a motor must be capable of applying a large torque to a fairly large X-ray frame to accelerate the frame to a high constant rate of rotation in a short time. As an indication of the speeds which are reached, sufficient data to produce an image can be collected in as little as one second. In a fourth generation CT scanner designated the Synerview 1200 which is commercially available from Picker International Inc. of Cleveland, Ohio, the rotating CT apparatus defines an aperture of sufficient diameter to allow a patient's torso to be inserted for scanning. Since the rotational inertia of this apparatus increases with distance from the axis of rotation, provision of this full body scanning capability results in rotating apparatus (including an X-ray tube) having a large inertia requiring high torques.

Belt linkages have an advantage in cost which is offset by their inability to provide sufficient torque for high speed computed tomography scanning. To provide sufficient torques to accelerate the Synerview 1200 scanner a motor having magnets mounted to the rotating frame and field coils mounted to the stationary gantry are used. This induction motor is more expensive than belt linkages but provides higher torques needed to rapidly accelerate the X-ray tube. The cost disadvantage of the induction motor is at least partly attributable to a complex mounting scheme for the motor windings, scanner bearing and motor magnets.

DISCLOSURE OF INVENTION

In accordance with the invention an improved motor is provided for moving the rotating portions of a computed tomography scanner. The disclosed motor provides high torque at reduced cost while taking up less space in the scanner than the space required for prior drive systems.

The scanner includes a source of X-rays for scanning a cross-section of a subject of interest and a mechanism for rotatably mounting the source for scanning so that X-rays radiate a cross-section of the subject from a number of directions thereby obtaining sufficient information for computed tomography reconstruction.

The disclosed invention includes an induction motor having a field generating portion and a field responsive portion with one of the two portions coupled to and rotating with the scanning source and the other of said two portions remaining stationary and mounted to support structure for the X-ray source. The motor is an integral part of the computed tomography scanner rather than a component coupled to the scanner via a belt or gear.

In a disclosed embodiment of the invention the improved motor provides motive force to a fourth generation computed tomography scanner. A rotating frame supports an X-ray tube for rotation about a patient. An array of detectors is fixed and circumscribes a patient aperture through which a patient's torso can be positioned. In this design the rotatable frame and stationary gantry are coupled by an annular bearing having a diameter greater than the patient aperture.

The preferred bearing has an elongated inner race connected to the rotating frame which extends along an axis co-incident with a patient's torso. The inner race serves not only as a coupling between the frame and gantry, but also supports the field responsive portion of the induction motor. In a disclosed design this portion includes a number of circumferentially spaced magnets which interact with fields created by stationary motor windings.

The motor windings and magnets are positioned in close proximity to each other across a narrow gap separating the frame from the gantry. Energization of the motor laminations causes interaction between the field generated by these laminations and the magnets supported by the frame. The force of this interaction causes relative rotation between the frame and gantry.

One advantage of the high torque motor is fast response permitting faster scan speeds. The motor can be built at a cost approximately the same as the prior art belt drive systems and less than the cost of the Synerview 1200 induction motor.

An additional advantage is a repositioning of the drive motor. This allows other CT scanning apparatus to be positioned in the location vacated by the prior art motor to produce a more compact design. Particularly, a cable take-up mechanism is moved to the space formerly occupied by the motor in the Synerview 1200 scanner. This reduces the inside diameter of the cable take-up and therefore reduces the moment of inertia of the CT system. From the foregoing it should be appreciated that one object of the invention is an improved computed tomography scanner employing a motor integrally constructed with the CT scanner apparatus. This and other objects, advantages and features of the invention will become better understood when a detailed description of the preferred embodiment of the invention is described in conjunction with the drawings.

BEST MODE FOR CARRYING OUT THE INVENTION

Figure 1:
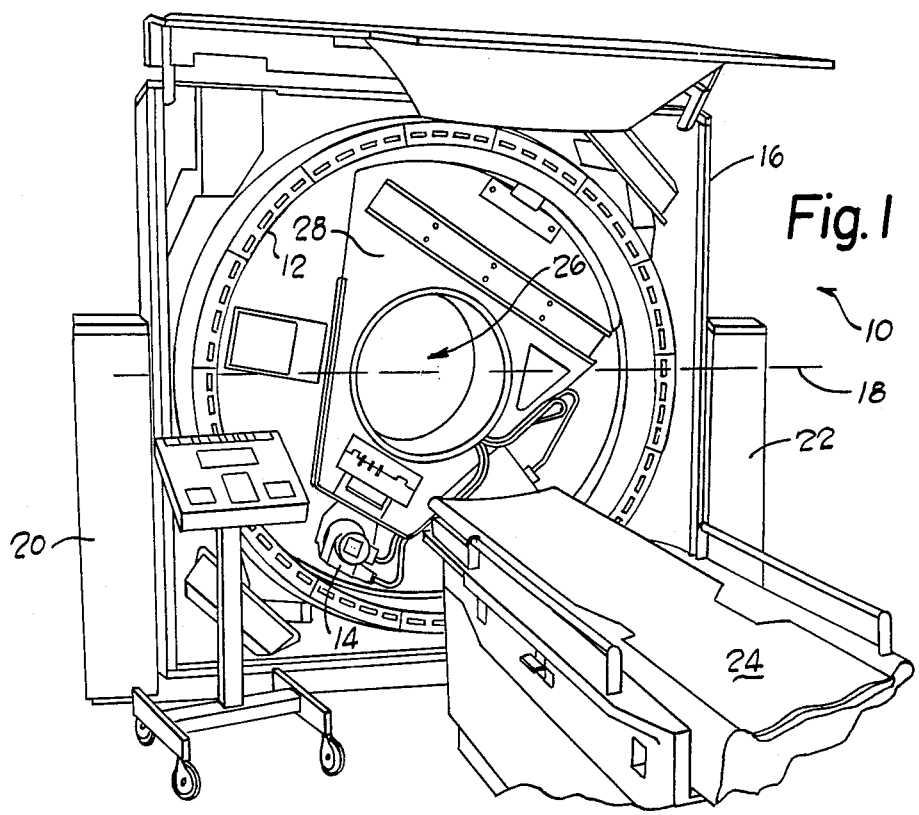
FIG. 1 is perspective view of a CT scanner with a front panel removed to illustrate an X-ray source and X-ray detector array.

Referring to the drawings and in particular FIG. 1, a computed tomography scanner 10 is illustrated. This scanner is a so-called fourth generation design scanner having a stationary array of detectors 12 and a X-ray source 14 rotatable in an orbital path. The detectors and source are mounted inside a housing 16 which can be pivoted about a pivot axis 18 to tilt the scanning plane. To provide this pivoting movement, two supports 20, 22 include a drive member (not shown) for tilting the housing about the pivot axis 18. A patient couch 24 is movable with respect to the scanning apparatus 10 to allow a supine patient to be positioned within a patient aperature 26 for computed tomography scanning.

Additional details concerning this computed tomography scanner may be obtained by reference to co-pending patent application Ser. No. 441,903 entitled "Computed Tomography Detection Method and Apparatus" to Zupancic et al assigned to Picker International Inc., assignee of the present invention. The disclosure of that copending application is incorporated herein by reference.

During computed tomography scanning the X-ray source 14 moves along an arcuate path inside the detector array 12 and irradiates a subject with x-radiation. A spread beam of radiation originating at the source 14 fans out and simultaneously impinges upon a number of detectors. In the Synerview 1200 CT scanner, detectors form a complete circular array and at any given time of a scan approximately one fourth or three hundred detectors are irradiated. The scanning motion of the source causes the group of detectors being irradiated to change with time so that in a typical scan all 1200 detectors are irradiated.

Figure 2:
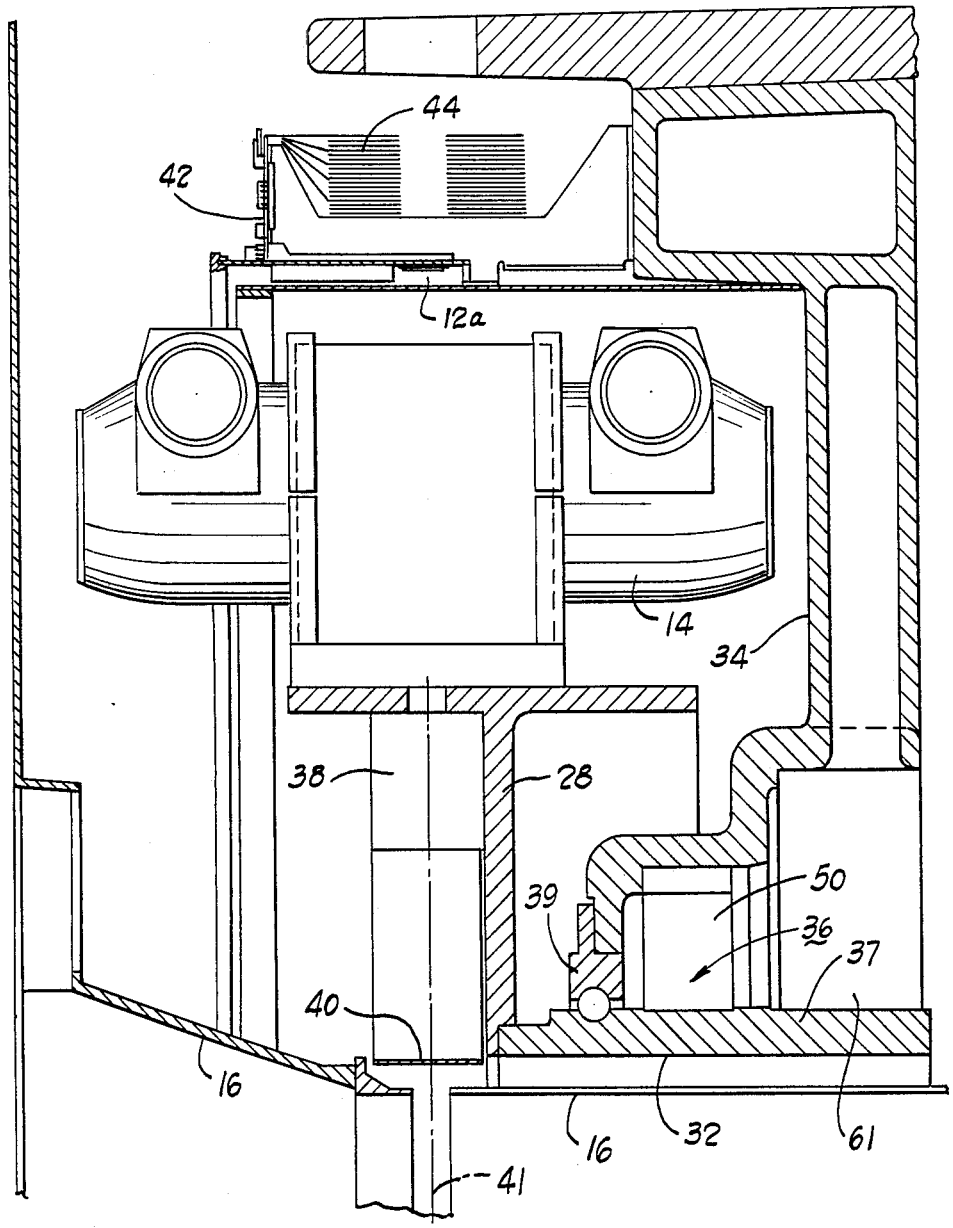
FIGS. 2 and 3 are axial sectional views on an enlarged scale of upper and lower portions of the CT scanner of FIG. 1.

The side sectional view of FIG. 2 illustrates the major components of the disclosed computed tomography scanner. An X-ray tube 14 is mounted to a rotating frame 28. The frame 28 is supported within a stationary gantry 34 along an annular bearing 36 which circumscribes the patient aperture 26. An inner race 37 of the bearing 36 extends along an axial direction to form a tube having a cylindrical inner surface 32. The frame 28 mounts directly to the inner race 37. An outer bearing race 39 extends a much shorter axial distance along the patient aperture 26. The outer race 39 is coupled to the fixed gantry 34.

Rotation of the frame 28 and X-ray tube 14 causes the tube, when energized, to direct x-radiation through a shutter 38 and collimator 40 and across a plane of interest 41. A patient is positioned within the aperture by moving the couch 24 so that a selected subject cross-section coincides with the plane 41 and is radiated by the rotating source 14.

Figure 3:
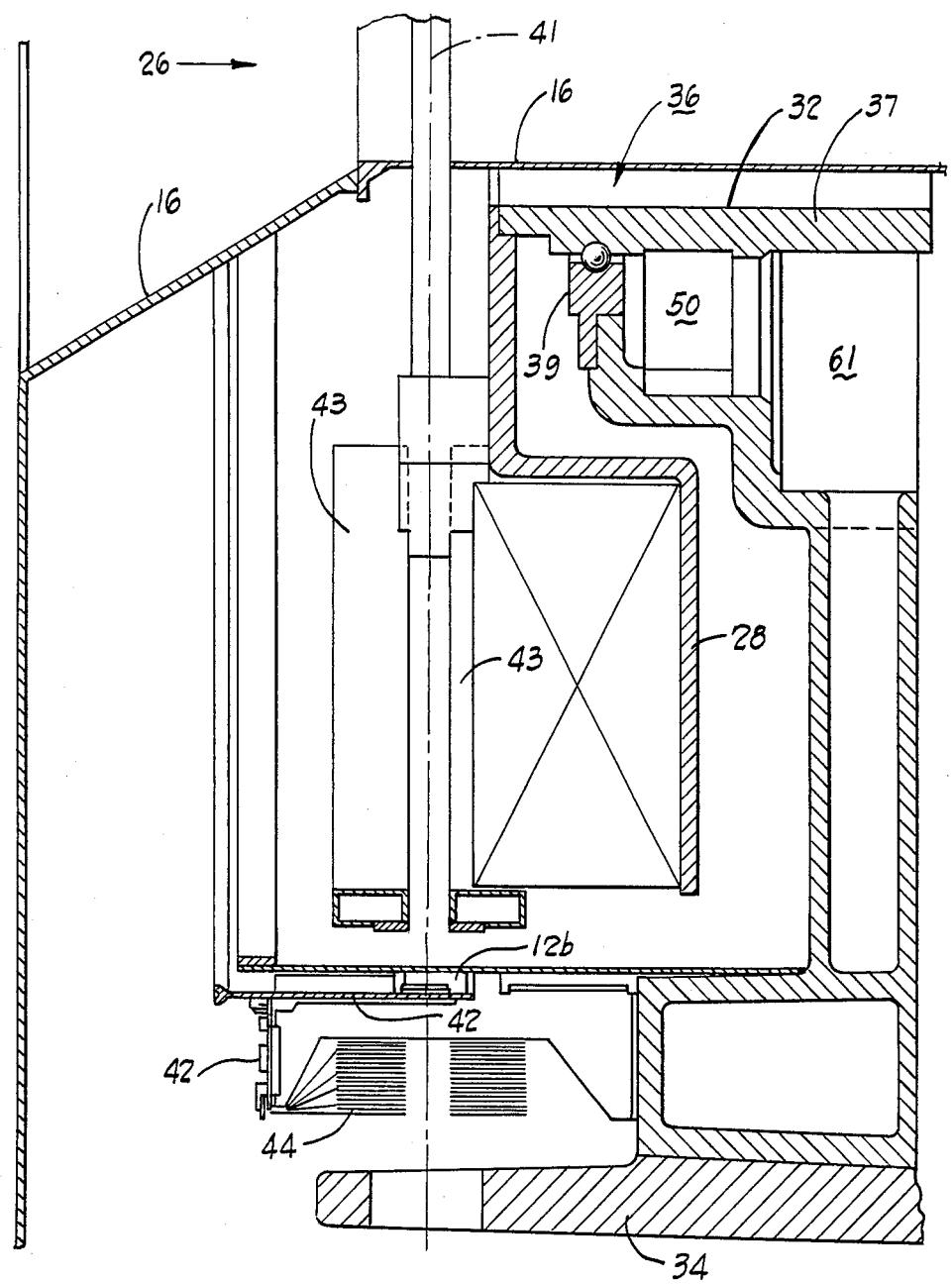

After traversing the subject, x-radiation from the tube 14 impinges upon the circular stationary array of detectors 12. Representative detectors 12a, 12b on opposed sides of the patient aperture are illustrated in FIGS. 2 and 3. To absorb radiation not in the plane of interest 41 a shield 43 mounted to the frame 28 absorbs stray radiation to minimize radiation reflections inside the scanner.

Via a mechanism known in the art, the detectors 12 convert x-radiation impinging upon the individual detectors 12a, b, etc. into electrical signals. In a particular system utilized in the Picker Synerview 1200 scanner circuitry mounted to printed circuit boards 42 (FIG. 3) supported by the gantry 34 generates a series of pulses wherein the pulse repetition rate from this circuitry is proportional to the x-radiation intensity impinging upon a particular detector within the array. Cables 44 route these electrical signals away from the stationary gantry to analyzing circuitry and ultimately to a specially programmed computer for computed tomography reconstruction.

Figure 4:
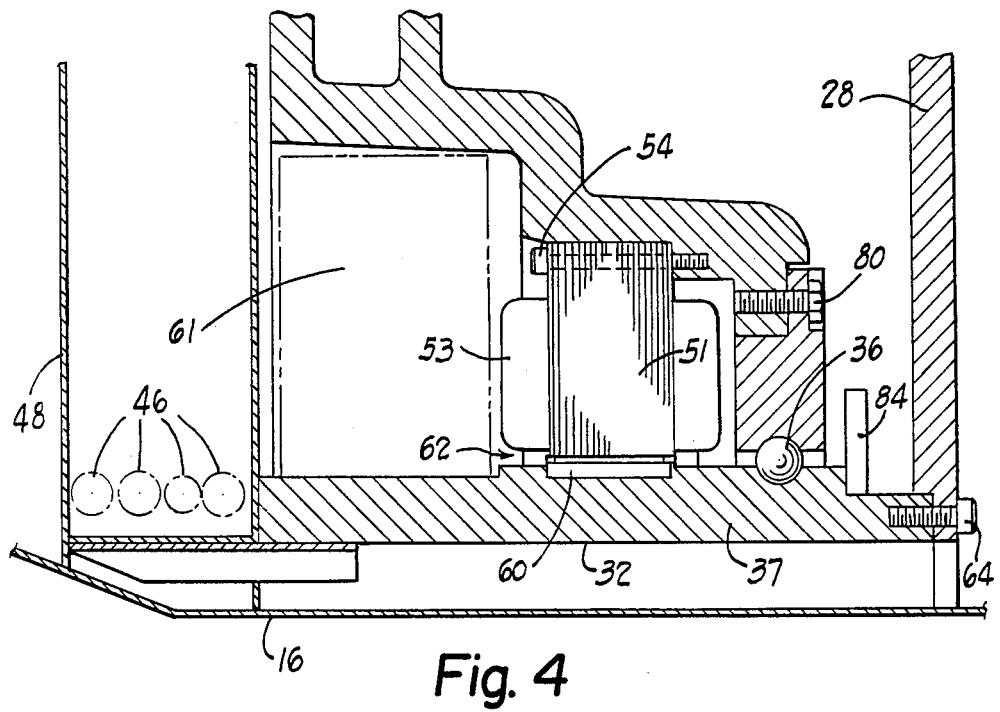
FIG. 4 is a further enlarged sectional view of a portion of the scanner shown in FIG. 2, particularly showing an axially elongated bearing supporting a frame for rotating said source.

The high voltages needed by the X-ray tube 14 for creating x-radiation are routed to the rotating tube via high voltage cables 46 (FIG. 4) supported within a cable take-up mechanism 48. As the rotating frame orbits the X-ray tube 14 about the patient, the high voltage cables 46 are unwound and as the tube rotates in an opposite direction these cables are rewound.

Figure 5:
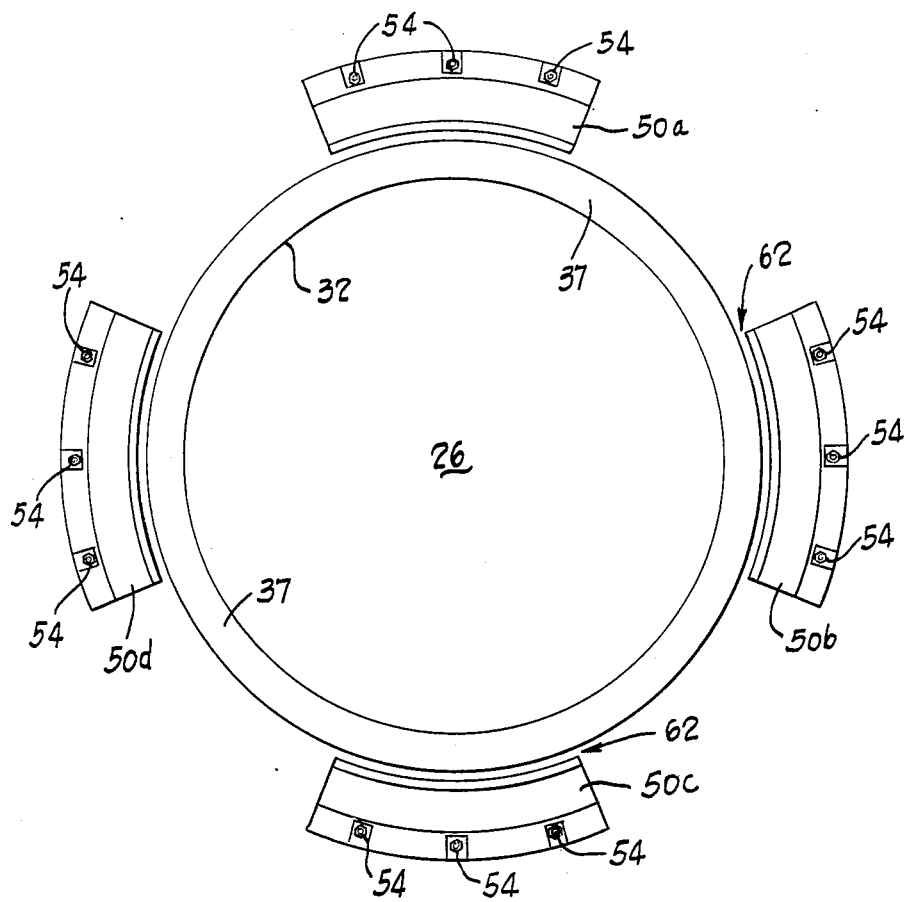
FIG. 5 is a front elevation schematic view showing the circumferential positioning of a four segment induction motor in relation to an inner race of said bearing.

In the disclosed scanner, a brushless variable speed three phase induction motor 50 causes relative rotation between the X-ray tube frame 28 and the gantry 34. The disclosed motor is divided into four segments 50a–d (FIG. 5) spaced about the patient aperture 26. One alternate embodiment of the motor is designed with three segments rather than four and a second alternate embodiment includes a continuous region of motor windings with no interruptions. Motor laminations 51 form a core for tightly wound conducting coils which when energized with an electrical signal to create a strong magnetic field resulting in high torque motor performance. The polarity of this field is reversed by reversing the polarity of coil energization. Each of the segments 50a–d are coupled to the stationary gantry 34 by threaded connectors 54.

A plurality of permanent magnets 60 are supported by the bearing inner race 37 within the magnetic field created by the coils 53. A small gap 62 between laminations and magnets results in good motor efficiency. A preferred embodiment has 60 magnets equally spaced about the aperture 26. When the motor laminations are energized, they create an electromagnetic field which interacts with the magnetic field of the magnets 60 causing attraction and repulsion between the magnets and motor laminations. This attraction and repulsion causes relative rotation between the gantry 34 and frame 28.

The motor windings are segmented into four portions with each portion connected to three amplifiers (not shown). Selective energization of the three amplifiers at frequencies variable from DC to 20 hertz results in acceleration and constant speed rotation of the frame at a speed of about 40 revolutions per minute. An optical sensor (not shown) monitors motion of the rotating frame and co-ordinates segment energization with this rotation.

Figure 6:
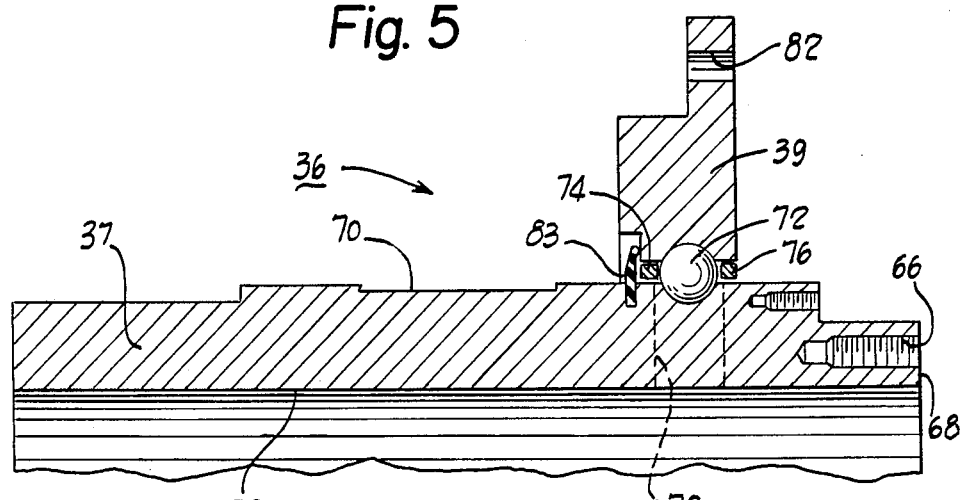
FIG. 6 is an enlarged sectional view of the main scanner bearing.

Turning now to FIG. 6, the bearing 36 is shown in greater detail. The inner race 37 extends axially a distance D of 11.625 inches. This inner race 37 supports the frame via twelve threaded connectors 64 which engage twelve equally spaced threaded openings 66 in a front surface 68 of the race 37. A rear portion of the race has a cylindrical inner surface 32 facing the patient aperture. An indentation 70 in an outer surface of this rear portion defines a region for mounting the magnets 60.

A bearing channel 72 supporting a plurality of ball bearings is bound top and bottom by the two races 37, 39 and on the sides by two cages 74, 76. The balls are inserted into the channel 72 through a fill hole 78 in the inner race 37 which is plugged after insertion of the balls. The entire bearing 36 is connected to the gantry 34 by threaded connectors 80 which engage twelve equally spaced holes 82 in the outer race 39. A bearing seal 83 prevents bearing grease from leaking out of the bearing to the vicinity of the motor 50.

As the motor 50 causes relative rotation between the frame and gantry, an optical encoder 84 mounted to the inner race 37 rotates with respect to an optical sensor (not shown) so that the angular orientation of the X-ray source 14 with respect to the detectors is known at all times. This information enables x-radiation intensity readings from the detectors to be analyzed and utilized in the known back projection technique to create a density mapping of the patient's cross-section of interest.

The motor 50 quickly accelerates the rotating frame to an appropriate speed and CT scanning takes place in a very short period of time, typically only a few seconds. Once scanning has been completed motor laminations are reverse energized to dynamically brake the frame 28. An emergency brake 61 stops frame motion in the event the dynamic motor braking does not do so. Once motion is stopped the motor 50 is energized to initiate scanning motion in an opposite sense and continued scanning takes place with rotation in first one sense and then in an opposite sense.

The present invention has been described with a degree of particularity but the construction of the disclosed motor and bearing need not be limited to a fourth generation CT scanner. It is the intent that the invention include all modifications and/or alterations falling within the spirit or scope of the appended claims.

We claim:

1. In a computed tomography scanner, apparatus comprising:
   a gantry supporting an annular array of detectors defining an X-ray scanning plane, said gantry having a through-passage with a generally cylindrical inside diameter;
   a frame coupled to the gantry for rotation relative to said gantry, said frame supporting an X-ray source for irradiating a subject of interest in said plane as said gantry and said frame rotate relative to each other;
   a bearing for rotatably coupling said frame and gantry, said bearing including a non-rotating and a rotating race member coupled directly to said gantry and frame respectively in rolling engagement with and spaced apart by a plurality of roller members to allow relative rotation between the rotating and non-rotating race member, said rotating race member defining a generally cylindrical surface surrounding the throughpassage defined by said gantry; and
   an induction motor for imparting relative rotation between the frame and gantry, said motor having field generating means coupled directly to said gantry and further having a number of magnets mounted directly onto the cylindrical surface of the rotating race member opposite said field generating means to respond to said field generating means and cause said relative rotation between the frame and gantry.

2. The apparatus of claim 1 wherein the frame defines an aperture of sufficient diameter to accommodate a patient's torso.

3. The apparatus of claim 1 where the elongated, generally cylindrical outer surface of the rotating race defines a channel facing the non-rotating race to define a region for positioning a plurality of ball bearings.

4. In a computed tomography scanner having a stationary array of detectors and a rotatably mounted source of X-rays for irradiating said array through a subject of interest apparatus comprising:
   a gantry for supporting said array so that said detectors encircle a subject throughpassage into which the subject is inserted for scanning;
   a rotatable frame for supporting said source so that X-rays from the source impinge upon said array of detectors after traversing said subject;
   an annular bearing of sufficient diameter to accommodate said subject, said bearing coupling said frame to said gantry through inner and outer race members extending axially along the throughpassage and mounted directly to said gantry and frame; and
   a motor having energizable field generating means stationary with respect to said subject directly mounted to the gantry and rotating magnets mounted directly to said inner race in juxtaposition to said field generating means to respond to energization of said field generating means and cause controlled rotation of said frame.

5. In a computed tomography scanner having a stationary support and rotating frame supporting an X-ray source for irradiating a subject of interest, a circular bearing surrounding a patient aperture for coupling the frame to the support comprising:
   an elongated inner race coupled to said frame and having a cylindrical inner surface and a cylindrical outer surface wherein one of said inner or outer surfaces supports magnets in proximity to one or more induction motor windings directly mounted to said stationary support;
   an outer race axially shorter than said inner race coupled to said inner race and mounted to said stationary support to support said inner race and said frame for rotation relative to said stationary support, and
   said inner and outer races defining a ball bearing channel into which ball bearings are inserted into rolling engagement with said inner and outer races.

6. The bearing of claim 5 where the inner race defines a ball bearing fill hole extending from the cylindrical inner surface of the inner race to said ball bearing channel defined by said inner and outer races.

* * * * *